United States Patent

Pasenok et al.

[11] Patent Number: 5,808,129
[45] Date of Patent: Sep. 15, 1998

[54] PROCESS FOR THE PREPARATION OF NOVEL STABILIZED PHOSPHORUS YLIDES

[75] Inventors: Sergej Pasenok, Liederbach; Wolfgang Appel, Kelkheim, both of Germany

[73] Assignee: Hoechst Aktiengesellschaft, Frankfurt, Germany

[21] Appl. No.: 756,886

[22] Filed: Dec. 2, 1996

Related U.S. Application Data

[62] Division of Ser. No. 640,161, Apr. 30, 1996, abandoned.

[51] Int. Cl.$^6$ .................................................. C07C 255/04
[52] U.S. Cl. ............................................................ 558/385
[58] Field of Search ................................ 568/17; 558/385

[56] References Cited

PUBLICATIONS

Y. Sheng et al., Synthesis, 1984, pp. 924–926.

*Primary Examiner*—Joseph McKane
*Assistant Examiner*—Ebenezer O. Sackey
*Attorney, Agent, or Firm*—Frommer Lawrence & Haug LLP

[57] ABSTRACT

Compounds of the formula (1)

$$Ph_3=CH—C(R)=Nu \quad (1)$$

wherein R is hydrogen, a $C_1$–$C_5$-alkyl, $C_1$–$C_3$-fluoroalkyl or perfluoroalkyl radical, an unfluorinated or fluorinated $C_6$–$C_{14}$-aryl radical or a group $OCH_3$; and Nu is S, Se, $C(CN)_2$, NH, PhN, PhNHN,

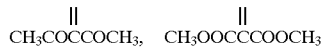

or a radical of the formulae (a), (b), (c), (d) or (e)

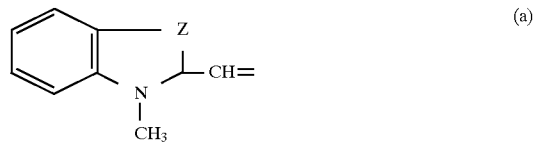
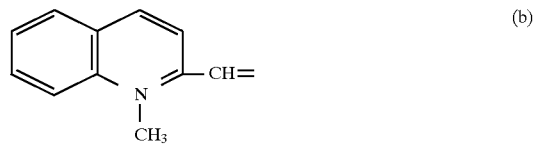
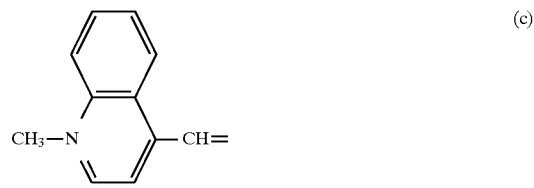
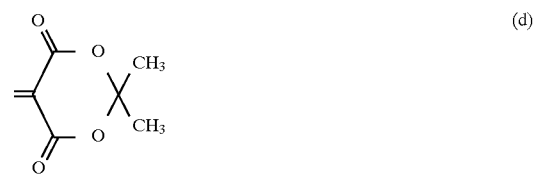
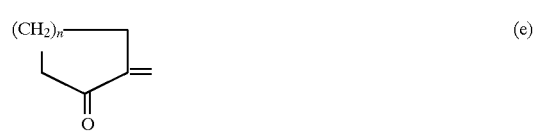

wherein Z is $C(CH_3)_2$, S or $N(CH_3)$ and n=1 or 2 (provided that the combinations R=Ar, SAlk or OAlk and Nu=NPh, and the combinations R=H, Alk or aryl and Nu=S are excluded) are disclosed, as well as methods for making them.

5 Claims, No Drawings

PROCESS FOR THE PREPARATION OF NOVEL STABILIZED PHOSPHORUS YLIDES

FIELD OF THE INVENTION

This application is a division of application Ser. No. 08/640,161, filed Apr. 30, 1996 now abandoned.

The present invention relates to novel stabilized phosphorous ylides and processes for their preparation. More particularly, the present invention relates to a process for substituting the carbonyl oxygen of 2-formyl- or 2-oxoalkylidenetriphenyl-phosphoranes (OATP) by other stabilizing groups to form novel compounds having an increased tendency to form complexes or compounds which absorb in the visible region of the spectrum.

BACKGROUND OF THE INVENTION

The contents of the references cited in the specification are hereby incorporated by reference.

Synthetically valuable 2-oxoalkylidenetriphenylphosphoranes (OATP) are usually prepared in two ways. Either by reaction of triphenylphosphine with α-haloketones and subsequent treatment of the resulting phosphonium salt with alkali metal hydroxide (M. I. Shevchuk et al., Zhurnal obshei Khimii, Vol. 40, N 1, pp. 48–57, 1970)

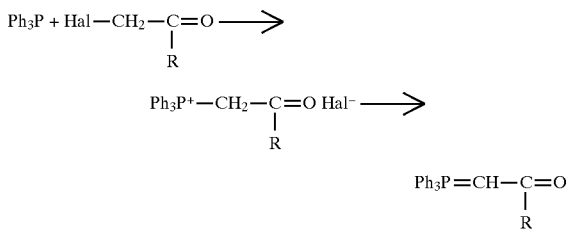

(R=alkyl, aryl or alkoxy) or by acylation of methylenetriphenylphosphorane with acyl chlorides (H. J. Bestmann et al., Chem. Ber. 95, 1513, 1962) or reactive carboxyl derivatives (Y. Sheng et al., Synthesis, 1984, p. 924–926).

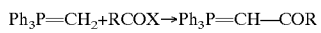

(R=alkyl, perfluoroalkyl or aryl; X=halogen, OR)

Some phosphorus ylides containing other stabilizing groups have been prepared by reaction of phenylethynyltriphenylphosphonium bromide (II) with anilines, enamines or acetoacetate (H. Hoffmann et al., Tetrahedron Letters N17, 1964, pp. 983–987)

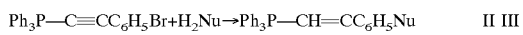      II III

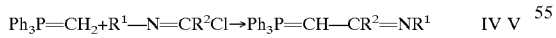      IV V or by acylation of methylenetriphenylphosphorane with imidoyl chloride (H. Yoshida et al., Synthesis 1977, pp. 626–628).

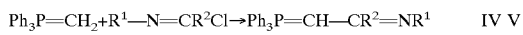      IV V $R^1$ (V)=Ar; $R^2$ (V)=Ar, SAlk, OAlk

Some 2-thioxoalkylidenetriphenylphosphoranes (VII) have been prepared by alkylation of triphenylphosphine with thio derivatives (VI) (EP-A-052 931);

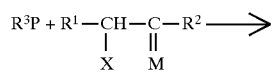

VI

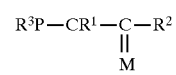

VII

M (VII)=S; $R^1$, $R^2$=H, Alk, Aryl

Except for the above mentioned processes, it has not been possible hitherto by the prior art to obtain phosphorus betaines having a stabilizing group other than the carbonyl oxygen in the β position. Phenylethynyltriphenylphosphonium bromide (II), imidoyl chlorides (IV) and the alkylated (thio)carbonyl compounds are usually accessible with great difficulty, so that the preparation of phosphorus betaines containing the above mentioned groups should be limited to only a few examples.

On the other hand, substitution of the oxygen by other groups having different steric and electronic properties would be an expedient way to modify organic compounds.

SUMMARY OF THE INVENTION

The object of the invention is thus to provide a simple and economic process which enables the carbonyl oxygen of 2-formyl- or 2-oxoalkylidenetriphenylphosphoranes (OATP) to be replaced by other stabilizing groups and, in this manner, the reaction behavior or, e.g., the complexing tendency of the entire molecule to be varied.

The present invention achieves this object and relates to novel compounds of the formula (1) and a process for their preparation $$Ph_3P=CH-CR=Nu \qquad (1)$$

wherein R is hydrogen, $C_1$–$C_5$-alkyl, a $C_1$–$C_5$-fluoroalkyl or perfluoroalkyl radical, an unfluorinated or fluorinated $C_6$–$C_{14}$-aryl radical or $OCH_3$; and Nu is S, Se, $C(CN)_2$, NH, PhN, PhNH—N=,

or a radical of the formulae (a), (b), (c), (d) or (e)

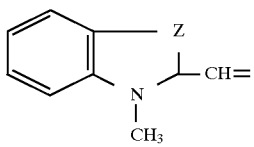      (a)

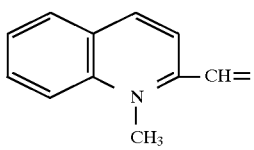      (b)

-continued

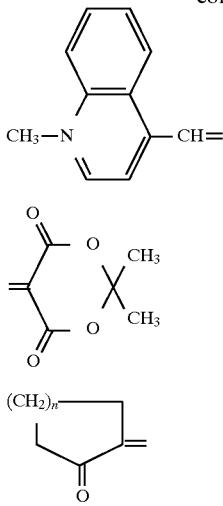

(c)

(d)

(e)

wherein Z is C(CH$_3$)$_2$, S or N(CH$_3$) and n=1 or 2; provide that the combinations R=Ar, SAlk, or OAlk and Nu=NPh, and the combination R=H, Alk, or aryl and Nu=S are excluded.

Compounds of the formula (1) are obtainable by first reacting 2-formyl- or 2-oxoalkylidenetriphenylphosphoranes with chlorinating agents to give compounds of the formula (2)

Ph$_3$P$^+$—CH=C(R)—Cl X$^-$  (2)

wherein X is Cl, Br or POCl$_2$, followed by reaction of compounds of the formula (2) with nucleophiles (Nu).

DETAILED DESCRIPTION OF THE INVENTION

Surprisingly, it has now been found that, in the reaction of 2-formyltriphenylphosphoranes or 2-oxoalkylidenetriphenylphosphoranes with a chlorinating agent, stable 2-chloroalkenylphosphonium salts of the formula (2) are formed. According to the known prior art, it would be expected here that these compounds react, with hydrogen exchange, to give the corresponding α-chloro ylides (D. B. Denny et al. J. Org. Chem. 27, 998 1962) or react, with oxygen exchange, to give the dichloroalkyltriphenylphosphonium salts.

The stoichiometric ratio of 2-formyl- or 2-oxoalkylidenetriphenylphosphoranes to the chlorinating agent used is, according to the invention, generally 1:1.5 to 1:2.

Chlorinating agents which are preferably used are POCl$_3$, PCl$_3$, COCl$_2$, (COCl)$_2$, SOCl$_2$ or other conventional chlorinating agents. The temperature in the chlorination reaction is in a range from 60° to 150° C., preferably in a range from 90° to 120° C., with a reaction time in the range from 30 to 90 minutes, in particular from 40 to 60 minutes.

The reaction proceeds in an organic, preferably chlorinated, solvent, such as carbon tetrachloride, chloroform or methylene chloride, but it can also be carried out without solvent. The yields of 2-chloroalkenylphosphonium salts are 80 to 100%, in particular >90%.

The phosphonium salts obtained in this manner can be reacted with various nucleophiles, such as Na$_2$S, Na$_2$Se, H$_2$C(CN)$_2$, 1,3,3-trimethyl-2-methylene-1,3-indole (Fischer base), CH$_3$COOCH$_2$COOCH$_3$, CH$_3$COCH$_2$COCH$_3$ or with PhNH$_2$, PhNHNH$_2$ and NH$_3$ and compounds of the formulae below:

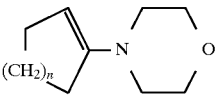

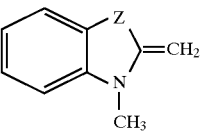

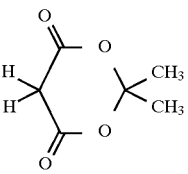

where Z is O, S, N(CH$_3$)$_2$, or C(CH$_3$)$_2$, CH=CH, to give novel stabilized Wittig ylides of the formula (1).

The yields of compounds of the formula (1) in this reaction are in the range from 50 to 90%, preferably in the range from 70 to 90%.

The reaction of compounds of the formula (2) with nucleophiles is carried out in organic solvents, such as methanol, ethanol, methylene chloride or acetonitrile. For this purpose, the appropriate nucleophile is employed in a stoichiometric or superstoichiometric proportion based on the triphenyl-β-chloroalkenylphosphonium salt used. In particular, the ratio of nucleophile to compounds of the formula (2) is in the range from 1:1 to 1:2.

The reaction time is in the range from 30 to 80 minutes, at a temperature in the range from 20° to 80° C., in particular from 20° to 40° C.

The novel compounds of the formula (1) have, in comparison with the corresponding compounds containing a carbonyl oxygen, a range of interesting properties. By replacing the carbonyl oxygen by sulfur, selenium or heterocyclic fragments, it is possible, for example, to obtain compounds having an increased tendency to form complexes or compounds which absorb in the visible region of the spectrum and which can therefore be used, e.g., as sensitizers for silver halides in photography, as precursors in the preparation of β-substituted cyanine dyes and for the synthesis of conjugated systems and as synthons for the preparation of various heterocycles.

EXAMPLE 1

Preparation of Triphenyl-(2-chloroalkenyl) Phosphonium Salts

In a three-neck flask equipped with thermometer, cooler and bubble counter, 20 mmol of the corresponding triphenyl-β-oxophosphorane and 40 mmol of POCl$_3$ are heated at 100° C. for 60 to 90 minutes. The excess of POCl$_3$ is distilled off in vacuo, the residue is washed three times with diethyl ether and dried in vacuo.

a. Triphenyl-(2-chloroprop-1-enyl)phosphonium dichlorophosphate:
   Yield: 92%
   Melting point: 105°–107° C.

b. Triphenyl-(2-chloro-3,3-difluoroprop-1-enyl) phosphonium dichlorophosphate:
   Yield: 94%
   Melting point: 150°–152° C.

C. Triphenyl-(2-chloro-3,3,3-trifluoroprop-1-enyl)
phosphonium dichlorooxyphosphate:
Yield: 91%
Melting point: 110°–112° C.

EXAMPLE 2

Preparation of Triphenylphosphoranylidenealkane-2-thiones 50 mmol of the corresponding triphenyl-β-chloroalkenylphosphonium salt are stirred together with 100 mmol of $Na_2S$ in 50 ml of methanol for one hour at 20° C. The reaction mixture is diluted with 100 ml of water and the organic phase is extracted twice with dichloromethane. The extract is dried over sodium sulfate and filtered and the organic solvent is distilled off in vacuo. The residue is recrystallized from a $CH_2Cl_2$:hexane mixture.

a. 3-(Triphenylphosphoranylidene)propane-2-thione
Yield: 89%
Melting point: 180°–182° C.
b. 1,1-Difluoro-3-(triphenylphosphoranylidene)propane-2-thione
Yield: 71%
Melting point: 146°–148° C.
c. 1,1,1-Trifluoro-3-(triphenylphosphoranylidene)propane-2-thione
Yield: 74%
Melting point: 162°–164° C.
d. 1-Phenyl-2-(triphenylphosphoranylidene)ethanethione
Yield: 84%
Melting point: 164°–166° C.

EXAMPLE 3

Preparation of 1,1-Difluoro-3-(triphonylphosphoranylidene)propane-2-selenone 50 mmol of triphenyl-(2-chloro-3,3-difluoroprop-1-enyl) phosphonium oxochloride are stirred with 100 mmol of $Na_2Se$ in 50 ml of methanol for one hour at 20° C. The reaction mixture is diluted with 100 ml of water, the organic phase is extracted twice with dichloromethane and dried over sodium sulfate. The solvent is filtered off and then distilled off in vacuo. The residue is recrystallized from a $CH_2Cl_2$:hexane mixture.

Yield: 52% Melting point: 149°–151° C.

EXAMPLE 4

Preparation of Triphenylphosphoranylidenealkylethylidelidene-malononitriles 50 mmol of the corresponding triphenyl-β-chloroalkenylphosphonium salt are stirred together with 50 mmol of malonodinitrile in 40 ml of ethanol and 100 mmol of triethylamine for one hour at 20° C. The precipitate is filtered off and the product recrystallized from ethanol.

a. 1-(Triphenylphosphoranylidene)methylethylidenemalononitrile
Yield: 88%
Melting point: 266°–268° C.
b. 2,2-Difluoro-1-(triphenylphosphoranylidene)methylethylidenemalononitrile
Yield: 72%
Melting point: 211° C.
c. 2,2,2-Trifluoro-1-(triphenylphosphoranylidene)methylethylidenemalononitrile
Yield: 90%
Melting point: 234°–236° C.
d. 1-(Triphenylphosphoranylidene)phenylethylidenemalononitrile
Yield: 61%
Melting point: 238°–240° C.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

What is claimed is:

1. A compound of the formula (1)

$$Ph_3P=CH-C(R)=Nu \qquad (1)$$

wherein:
R is hydrogen, a $C_1$–$C_5$-alkyl, $C_1$–$C_3$-fluoroalkyl or perfluoroalkyl group, an unfluorinated or fluorinated $C_6$–$C_-$-aryl group or a $OCH_3$ group; and
Nu is $C(CN)_2$
provided that the combinations R=Ar, or Oalk and Nu=NPh, and the combination R=H, Alk, or aryl are excluded.

2. The compound of claim 1 which is 1-(triphenylphosphoranylidine)methylethylidenemalononitrile.

3. The compound of claim 1 which is 2,2-difluoro-1-(triphenylphosphoranylidene)methylethylidenemalononitrile.

4. The compound of claim 1 which is 2,2,2-triffloro-1-(triphenylphosphoranylidene)methylethylidenemalononitrile.

5. The compound of claim 1 which is 1-(triphenylphosphoranylidene)phenylethylidenemalononitrile.

* * * * *